(12) United States Patent
Canady

(10) Patent No.: US 7,611,510 B2
(45) Date of Patent: Nov. 3, 2009

(54) APC DUAL MODE LEEP APPARATUS AND METHOD

(76) Inventor: Jerome Canady, 1119 Jefferson St., McKeesport, PA (US) 15132

( * ) Notice: Subject to any disclaimer, the term of this patent is extended or adjusted under 35 U.S.C. 154(b) by 567 days.

(21) Appl. No.: 11/278,816

(22) Filed: Apr. 6, 2006

(65) Prior Publication Data

US 2006/0229600 A1    Oct. 12, 2006

Related U.S. Application Data

(60) Provisional application No. 60/668,777, filed on Apr. 6, 2005.

(51) Int. Cl.
*A61B 18/14* (2006.01)
(52) U.S. Cl. .......................... 606/45; 606/49
(58) Field of Classification Search ............ 606/27, 606/41, 45–47, 49, 113
See application file for complete search history.

(56) References Cited

U.S. PATENT DOCUMENTS

| | | |
|---|---|---|
| 4,040,426 A | 8/1977 | Morrison |
| 4,781,175 A | 11/1988 | McGreevy |
| 5,108,392 A | 4/1992 | Spingler |
| 5,122,138 A | 6/1992 | Manwaring |
| 5,207,675 A * | 5/1993 | Canady .................. 606/40 |
| 5,217,460 A | 6/1993 | Knoepfler |
| 5,318,448 A | 6/1994 | Garito et al. |
| 5,330,469 A | 7/1994 | Fleenor |
| 5,464,405 A | 11/1995 | Fujitsu |
| 5,542,945 A | 8/1996 | Fritzsch |
| 5,554,159 A | 9/1996 | Fischer |
| 5,556,397 A | 9/1996 | Long et al. |
| 5,603,712 A | 2/1997 | Koranda et al. |
| 5,658,281 A | 8/1997 | Heard |
| 5,720,745 A | 2/1998 | Farin et al. |
| 5,746,739 A | 5/1998 | Sutter |
| 6,149,620 A | 11/2000 | Baker et al. |
| 6,197,026 B1 | 3/2001 | Farin et al. |
| 6,231,574 B1 | 5/2001 | Posthuma |
| 6,267,759 B1 * | 7/2001 | Quick .................. 606/47 |
| 6,283,963 B1 | 9/2001 | Regula |
| 6,293,946 B1 | 9/2001 | Thorne |
| 6,416,513 B1 | 7/2002 | Dresden |
| 6,458,124 B1 | 10/2002 | Garito |
| 6,458,125 B1 | 10/2002 | Cosmescu |
| 6,464,701 B1 | 10/2002 | Hooven et al. |
| 6,558,379 B1 | 5/2003 | Batchelor et al. |
| 6,585,735 B1 | 7/2003 | Frazier et al. |
| 6,743,228 B2 * | 6/2004 | Lee et al. ............... 606/47 |
| 2002/0095152 A1 | 7/2002 | Ciarrocca |
| 2007/0034211 A1 * | 2/2007 | Hug et al. ............ 128/876 |

* cited by examiner

*Primary Examiner*—Lee S. Cohen
*Assistant Examiner*—Samantha Muro
(74) *Attorney, Agent, or Firm*—24IP Law Group; Timothy R. DeWitt

(57) ABSTRACT

A multi-mode LLETZ or LEEP device for performing LLETZ surgery and argon plasma coagulation using a single device is disclosed. The disclosed device has a body with a channel therein and movable arms having a wire therebetween at a distal end of the body such that the arms may be extended to perform conventions LLETZ surgery or may be moved together for performing argon plasma or beam coagulation.

13 Claims, 6 Drawing Sheets

APC DUAL MODE LEEP APPARATUS AND METHOD

CROSS-REFERENCE TO RELATED APPLICATIONS

The present application claims the benefit of the filing date of U.S. Provisional Application Ser. No. 60/668,777 entitled "APC Dual Mode Leep Apparatus and Method," and filed on Apr. 6, 2005 by inventors Jerome Canady.

The above cross-referenced related application is hereby incorporated by reference herein in their entirety.

STATEMENT REGARDING FEDERALLY SPONSORED RESEARCH OR DEVELOPMENT

Not applicable.

BACKGROUND OF THE INVENTION

1. Field of the Invention

The present invention relates to surgical devices capable of performing both argon plasma coagulation and traditional electrocautery during loop electro-surgical excision and other procedures.

2. Brief Description of the Related Art

A loop electro-surgical excision procedure, known as LEEP, is a procedure performed to treat cervical dysplasia, which is an abnormal tissue growth in the cervix. This procedure also is known as a Large Loop Excision of the Transformation Zone, which often is abbreviated as LLETZ or LEETZ. In the LEEP procedure, a wire loop is used to remove the abnormal tissue from the cervix. The wire loop is connected to an electrosurgical unit and is used to scoop out the abnormal tissue in one piece and seal any bleeding blood vessel via electrocautery. The procedure allows the healthcare provider to locate and remove the cervical dysplasia in one procedure, thereby saving the step of taking a sample piece of tissue (a biopsy) before removing the tissue by other methods, such as by freezing it or by performing a surgical cone procedure.

A variety of LLETZ devices are known and have been used for these procedures. These known devices typically have an elongated body with a pair of arms extending perpendicular to the body at one end. A wire electrode extends outward from each of the arms thereby forming a wire loop at the end of the device. The body further has means for connecting the wire loop to an electrosurgical generator. The arms can be of a variety of lengths and sizes. Examples of such conventional LLETZ electrodes are Valleylab's single use LLETZ electrodes catalog nos. E1559, E1560, E1561, E1562, E1565, E1566 and E1567. In these Valleylab devices, the arms are fixed in positions approximately perpendicular to the device body to thereby create or support the sire loop. In other known LLETZ devices, the arms are fixed in positions other than perpendicular to the body. Other embodiments of LLETZ devices are disclosed in U.S. Pat. Nos. 5,318,448 and 5,554,159, which are hereby incorporated by reference in their entirety.

Another embodiment of a known LLETZ device is disclosed in U.S. Pat. No. 6,416,513 to Dresden, which is hereby incorporated by reference in its entirety. In this embodiment, the device has a moveable arm that may be adjusted by the surgeon to adjust the concavity of the wire loop electrode.

One of the risks of the LLETZ procedure is heavy bleeding. Heretofore, a variety of means have been used to control such heavy bleeding. For example, traditional electrocautery may be performed using the wire loop electrode in the device or a paste may be applied to the tissue to reduce bleeding. Other known means of controlling bleeding have likewise been used.

Controlling or arresting blood loss is of high priority during surgery so as to avoid or minimize the necessity of introducing foreign blood or blood products into a patient. This has increased in importance due to concern over contamination of the blood supply by viral agents which cause, for example, acquired immune deficiency syndrome (AIDS), hepatitis, and the like.

Standard means for controlling traumatic and surgical blood loss are electrosurgical generators and lasers, which respectively direct high-frequency electrical currents or light energy to localize heat in bleeding vessels so as to coagulate the overlying blood and vessel walls.

Argon beam coagulators, also known as Argon Plasma Coagulators (APC), additionally have been demonstrated to be effective tissue coagulators. Examples of argon beam coagulators for use in open surgery can be found in U.S. Pat. No. 4,040,426 to Morrison and U.S. Pat. No. 4,781,175 to McGreevy. Argon beam coagulators for use rigid and flexible endoscopy also are known. An example of a device for flexible endoscopy may be seen in U.S. Pat. No. 5,207,675 to the present inventor. In some embodiments in that patent, the inventor disclosed dual modality devices that could be used either for argon plasma coagulation or for traditionally electrocautery in an endoscopic environment. The inventor also disclosed an embodiment having the dual modality of argon plasma coagulation and endoscopic biopsy forceps. In that embodiment, argon plasma coagulation could be used by a surgeon while the biopsy forceps were withdrawn inside the flexible endoscopic tube. The biopsy forceps could then be extended and used, but argon plasma coagulation was not performed with the biopsy forceps extended from the end of the tube.

With respect to LLETZ procedures, the conventional LLETZ device may be removed from the patient and an argon beam coagulator may be inserted to control bleeding.

While these known LLETZ devices and various means of controlling bleeding have been used in the past with varying degrees of success, a need exists for a single device that can perform a traditional LLETZ procedure and use argon beam coagulation to quickly control bleeding without repeated insertion and removal of instruments.

SUMMARY OF THE INVENTION

In a preferred embodiment, the present invention comprises an elongated body having a first channel therein, a movable arm having a second channel therein, said second channel being connected to said first channel, a wire within said first channel, said wire having a loop at a distal end and a portion of said loop being within said second channel, means for connecting said first channel to a source of an inert, ionizable gas; means for connecting said wire to a source of RF energy.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
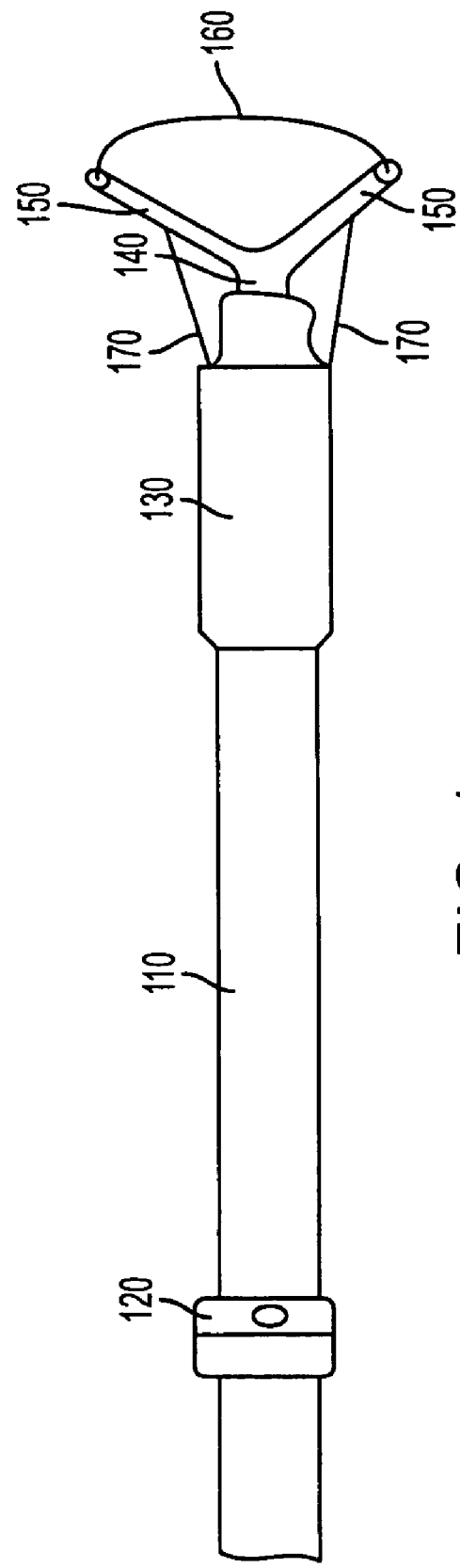
FIG. 1 is a side view of a preferred embodiment of an APC dual mode LLETZ in a configuration for removing tissue in accordance with the present invention.

A preferred embodiment of the present invention incorporates moveable arms, a retractable electrode, tubes surrounding the electrode, and an inert ionizable gas such as argon to provide a single device capable of performing both traditional LLETZ surgery and argon plasma (or beam) coagulation. A preferred embodiment will be described in connection with FIGS. 1-7.

The device has a cylindrical or tubular body 110 having a collet, handle, plug or other means 120. For LLETZ surgery, it may be preferable for the body 110 to be rigid or semi-rigid, but for other types of surgery, such as endoscopic or laparoscopic surgery, the body 110 may be flexible. The body 110 further has means for connecting the device to an electrosurgical generator and a source of an inert, ionizable gas such as argon. The means for connecting to the electrosurgical generator and/or argon gas may be through or part of the collet, handle or plug 120 or may be otherwise. The collet 120 is displaced from the distal end of the body 110 by a distance sufficient for the collet 120 to remain outside the patient's body and be accessible to the surgeon during surgery. At the distal end of the body 110, there are two adjustable or moveable arms 150 that are connected to the body 110 via a hinge 530, hinges or other means that would permit the arms to rotate toward and away from each other in a plane. Each arm 150 is connected to a collet 130 by a rod, wire or other means 170. When the collet 130 is moved by the surgeon along the length of the body 110 by means of rotating the collet or otherwise, the rods 170 pull the arms 150 apart or push them together depending on which direction the collet 130 is moved. In an embodiment in which wires 170 are used rather than rods, the arms 150 may be biased toward one position, such as together, and the surgeon may used the collet 130 to pull the arms 150 apart via the wires 170.

Within the body 110, there is a channel 220, within which there is a wire 210 for conducting electricity. The wire is formed of a conductive material, but preferably is formed from tungsten or tungsten and molybdenum. The channel may be formed integral with the body or may be a flexible plastic tube. The channel extends along the length of the body 110 at least from the collet or plug 120 to the distal end of the body, where the channel or tube splits into two channels, one along each arm. The channel along the arms may be formed integral with the arms or may be attached to the arms. For example, the channel 220 and the split channels along the arms may all be formed of flexible tubing that is attached or connected to the arms 150.

Figure 2:
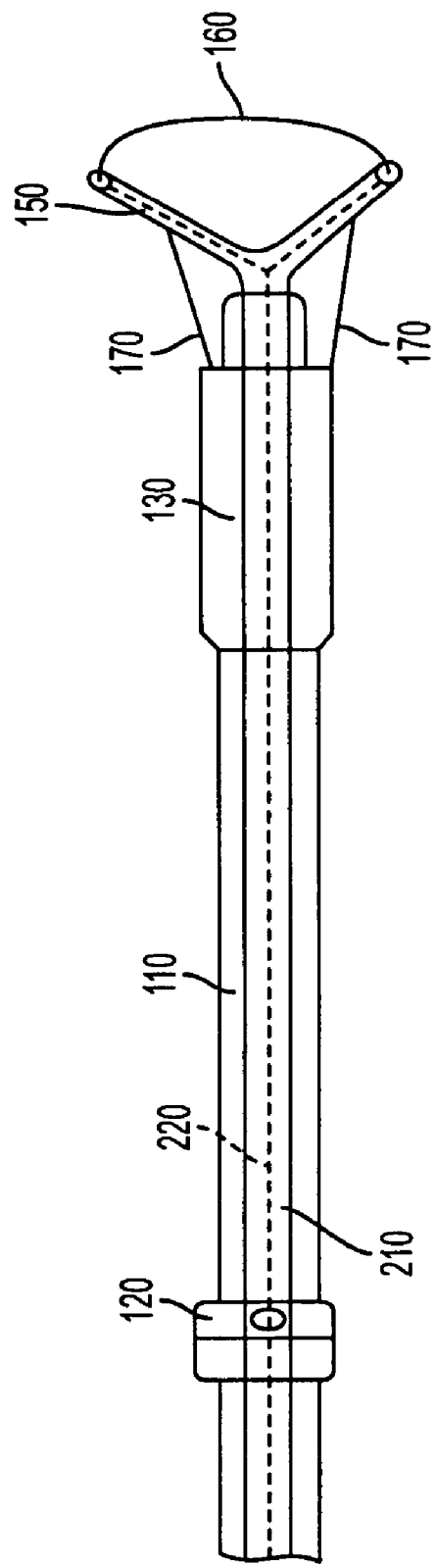
FIG. 2 is a cross-sectional view of a preferred embodiment of an APC dual mode LLETZ in accordance with the present invention.
Figure 3:
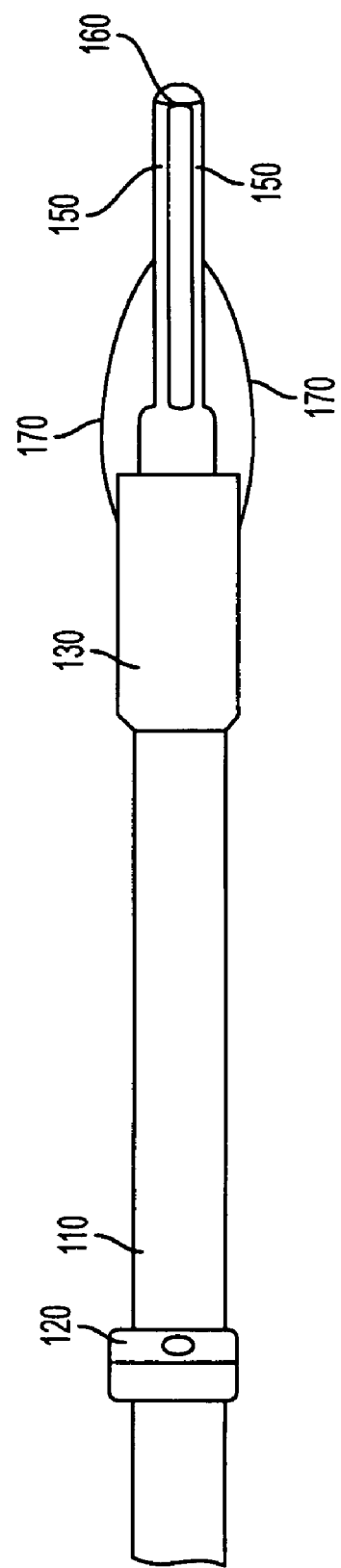
FIG. 3 is a side view of a preferred embodiment of an APC dual mode LLETZ in a configuration for performing argon plasma coagulation in accordance with the present invention.
Figure 4:
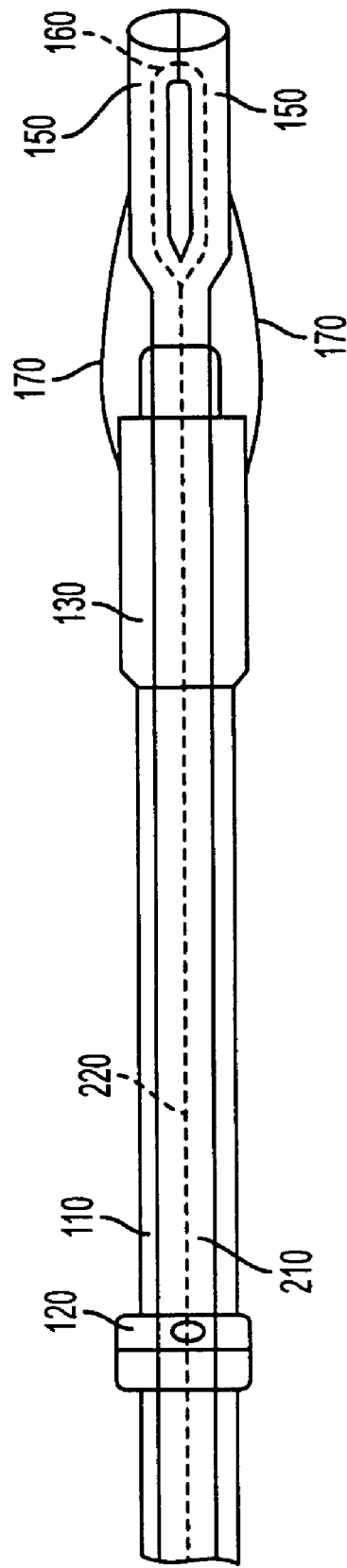
FIG. 4 is a cross-sectional view of a preferred embodiment of an APC dual mode LLETZ in a configuration for performing argon plasma coagulation in accordance with the present invention.
Figure 5:
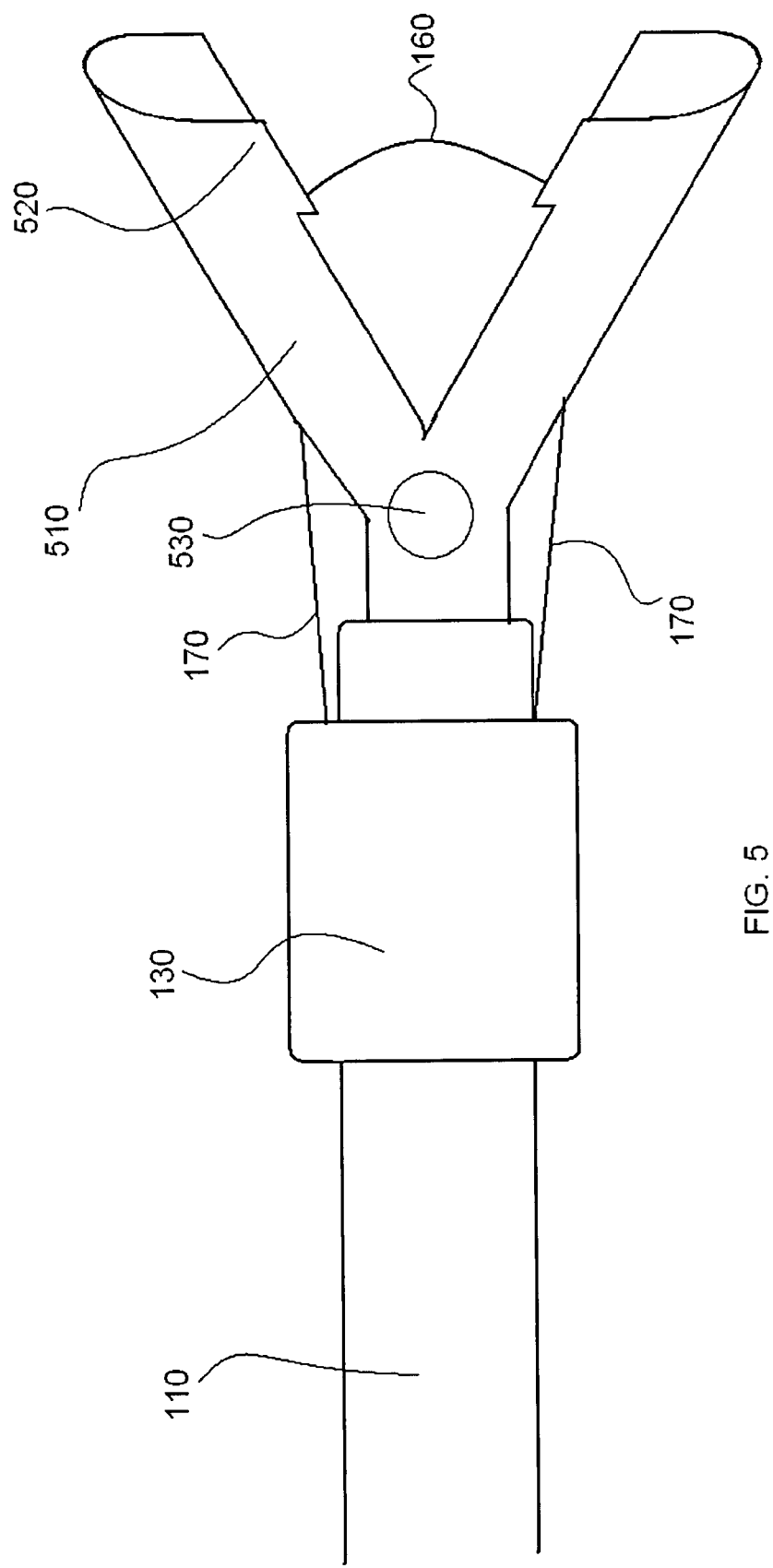
FIG. 5 is a side view of a preferred embodiment of moveable arms of an APC dual mode LLETZ device in accordance with the present invention.
Figure 6A:
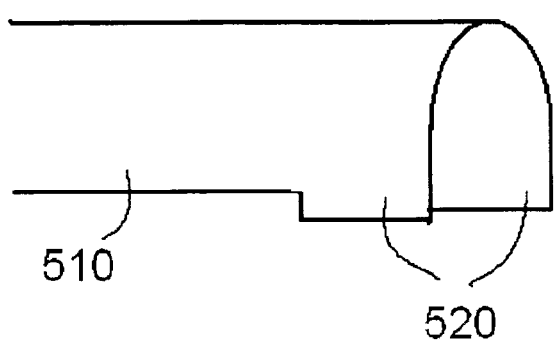
FIGS. 6(a), (b), (c) and (d) are side and end views of a preferred embodiment of a pair of arms of a preferred embodiment of a LLETZ device in accordance with the invention.
Figure 6B:
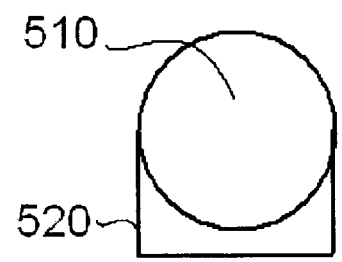
Figure 6C:
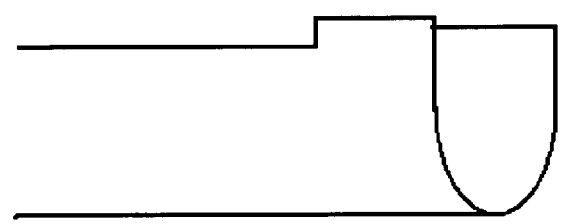
Figure 6D:
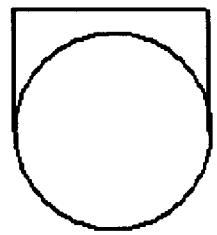

The wire 210 within the channel 220 likewise extends along the length of the body form the collet or plug 120 to the distal end of the body 110. At or near the distal end of the body 110, the wire 210 has a loop 160 that extends through the split channels at the arms 150. The wire 210 is movable within the channel 220 via collet, handle, or plug 120. When the arms are in a position extending away from one another such as is shown in FIGS. 1-2, the loop 160 at the distal end of the wire 210 has an appearance and use similar to a conventional LLETZ device. When the arms are closed, however, the loop 160 may be withdrawn as shown in FIGS. 3-4 such that argon gas may flow down the channel 220 and may be sued to perform argon plasma coagulation by electrifying the wire 210 while argon gas is flowing through the tube.

The preferred embodiment may further have enclosure means on the arms 150 or the split channels for enclosing the loop 160 during argon plasma coagulation as shown in FIGS. 5 and 6(a)-(d). In a preferred embodiment, the enclosure means on each arm or split channel has a tubular portion 510 and a half-cylinder portion 520. When the arms 150 are moved together and the wire is withdrawn, the semi-cylinder portions 520 for a channel such that the loop 160 is approximately 1 mm inside the end of the channel. The enclosure means may be formed as part of the arms 150, part of the split channel, or as attachments to either the arms or the split channels. The enclosure means preferable is formed from a heat resistant material such as a ceramic material.

In other embodiments, the collet, handle or plug 120 may be combined with the collet 130 such that the wire 210 moved out or in along with the movement of the arms 150 out or in. Further, the device may include safety means to prevent or prohibit the flow of argon gas while the arms are in the extended LLETZ position. In still other embodiments, the invention may have one moveable arm that extends away from or together with either a fixed arm or the body 110.

Other embodiments adapt the present invention for minimally invasive surgery such as laparoscopy or endoscopy. Such adapted embodiments may be used or adapted to be used with any device for minimally invasive surgery, such as a colonoscope, laparoscope, thoroscope, etc. In such embodiments, the body 110 may be flexible and of a length and a diameter to permit the device to be inserted into the particular scope far enough that the distal end of the device extends out of the distal end of the scope. For example, the diameter would be small enough to be inserted into the working channel of an endoscope. Such a diameter may be 5 mm or less depending on the type of endoscope.

To insert the device into the scope, the surgeon or other operating room personnel would place the arms in the "in" or "together" position and then insert the distal end of the device into an opening in a channel in the scope. The elongated body 110 of the device would then be fed into the scope until the distal end of the device protrudes from the channel opening at the distal end of the scope. Once outside the distal end of the scope, the arms may be opened for electrocautery or "scooping" of tissue or the arms may remain or be closed for performing argon plasma coagulation. The device may be manipulated within the endoscope, i.e., moved in and out of the channel or rotated within the channel, by any means, such as by holding a portion of the body, collet or handle that is outside the opening at the proximal end of the endoscope.

While the foregoing embodiments have been described as having a pair of moveable arms, an alternative embodiment would have only one moveable arm. Such an embodiment would be akin to having a pair of arms one of which either is integral with the channel in the body or remains substantially parallel to the channel in the body while the other arm is moveable away from the body. Such alternate embodiment will be apparent to those of skill in the art from the foregoing disclosure.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

The invention claimed is:

1. A surgical device comprising:
   an elongated body having a first channel therein;
   a first movable arm connected to said elongated body having a second channel therein, said second channel being in fluid communication with said first channel;
   a second movable arm having a third channel therein, said third channel being in fluid communication with said first channel
   means for moving said first and second movable arms between first and second positions, said second position being extended at least partially away from said body;
   a wire within said first channel, said wire having a loop at a distal end and a portion of said loop being within said second channel and a portion of said loop being within said third channel channel;
   a first plug for connecting said first channel to a source of an inert, ionizable gas;
   a second plug for connecting said wire to a source of RF energy; and
   enclosure means at a distal end of said second channel and said third channel for enclosing said loop when said arms are in a closed position.

2. A surgical device according to claim 1 wherein said inert ionizable gas comprises argon.

3. A surgical device according to claim 1 wherein said wire is moveable within said first channel.

4. A surgical device according to claim 3 wherein said wire is moveable within said second channel.

5. A surgical device according to claim 1 where said first channel comprises a flexible tube.

6. A surgical device according to claim 1 where said second channel comprises a flexible tube.

7. A surgical device according to claim 1 wherein said means for moving said arm comprises a collet.

8. A surgical device according to claim 1 wherein said elongated body is flexible.

9. A surgical device according to claim 1 wherein said elongated body comprises a flexible tube.

10. A surgical device according to claim 1 where said elongated body has a diameter of less than 5 mm.

11. A surgical device comprising:
    an elongated body having a channel therein;
    a pair of movable arms connected to said body near a distal end of said body, each of said movable arms having a channel in fluid communication with said channel in said body;
    means for moving said movable arms between first and second positions, said arms being substantially adjacent one another when in said first position and said arms extending at least partially away from one another when in said second position;
    a wire within said channel in said body, said wire having a loop at a distal end and different portions of said loop being within said channel within each of said arms;
    a first plug for connecting said channel in said body to a source of an inert, ionizable gas; and
    a second plug for connecting said wire to a source of RF energy,
    wherein said movable arms and said distal end of said body may be inserted into an endoscope when said movable arms are in said first position.

12. A surgical device according to claim 11 wherein said body is flexible.

13. A surgical device according to claim 11 wherein said body is rigid.

* * * * *